United States Patent [19]

Choyce et al.

[11] 4,087,866

[45] May 9, 1978

[54] INTRAOCULAR LENS

[75] Inventors: D. Peter Choyce, Westcliff-on-Sea; Mohammed Jalie, London, both of England

[73] Assignee: Coburn Optical Industries, Inc., Muskogee, Okla.

[21] Appl. No.: 790,915

[22] Filed: Apr. 26, 1977

[51] Int. Cl.² ............................ A61F 1/16; A61F 1/24
[52] U.S. Cl. ........................................................ 3/13
[58] Field of Search ...................... 3/13, 1; 351/160

[56] References Cited

FOREIGN PATENT DOCUMENTS 959,314  3/1957  Germany ................................. 3/13

OTHER PUBLICATIONS

"The Mark VI, Mark VII and Mark VIII Choyce Anterior Chamber Implants" by D. Choyce, Proceedings of the Royal Society of Medicine, vol. 58, Sep. 1965, pp. 729–731.

Primary Examiner—Ronald L. Frinks
Attorney, Agent, or Firm—Leon E. Tenenbaum

[57] ABSTRACT

An intraocular lens for implantation in the anterior chamber of the human eye is provided. The lens is convexo-planar with the planar surface facing the cornea.

3 Claims, 3 Drawing Figures

INTRAOCULAR LENS

FIELD OF INVENTION

This invention relates to ophthalmology, and more particularly, to a new type of intraocular lens for correcting optic defects in aphakia and restoring binocular vision.

THE PRIOR ART

The use of intraocular lenses in correcting the optic defects of aphakia is common, and many lenses have been developed for such purposes. Examples of such lenses are disclosed in U.S. Pat. nos. 3,971,073; 3,975,779; 3,979,780; 3,986,214; 3,994,027; 3,996,626 and 3,997,627. The lenses now in use or disclosed in these patents are adapted for insertion in the anterior chamber of the eye, i.e., the chamber between the cornea and iris, directly in front of the pupillary opening. Hereinafter, the term lens will refer to an intraocular lens positioned in the anterior chamber of the eye.

In the past, as can be noticed from the above-mentioned patents, the problem with these lenses has been their implantation. New developments in the structures of securing means for the lenses and the increasing skills of the surgeons have substantially eliminated the problem of implantation.

The lenses now in use are either biconvex or planar convex, but previously little or no consideration has been given to the shape of the lens in the fabrication of such lenses. The planar convex lenses in which the planar surface faces the posterior of the eye, i.e., the iris, appear to be preferred, and Binkhorst in Ophthalmic Surgery 6 (3), 17–31 (1975), has stated that such lenses are practically aplanatic, i.e. without spherical aberration when compared to biconvex lenses. Most of the lenses disclosed in the above-mentioned patents are planar-convex with the planar surface facing the iris.

Although such planar-convex lenses are an improvement over the biconvex type, they are not free of problems. Spherical aberration, although reduced, is still present, and a tilting or displacement of the lens frequently causes some dislocation of the refracted pencil of rays resulting in astigmatism. The planar-convex lens when inserted with the planar surface facing the iris also fails to provide the proper magnification.

THE PRESENT INVENTION

It is accordingly an object of the present invention to provide a lens which will most closely approximate the function of the natural lens that has been replaced.

It is another object of the present invention to provide a lens which has no greater or less spherical aberration than the natural lens that has been replaced.

It is a further object of the present invention which when tilted or otherwise dislocated will not effect the refracted pencil of rays as much as in presently available intraocular lenses.

It is still another object of the present invention to provide a lens whose power will focus the image on or in front of the retina.

Other objects will appear from the discussion which follows.

The objects are acheived by a planar-convex lens in which the convex surface faces the posterior of the eye, and the lens is so positioned that the convex surface does not come into direct contact with the iris.

The features of the present invention will be better understood from the description which follows, taken in conjunction with the drawings.

DESCRIPTION

Figure 1:
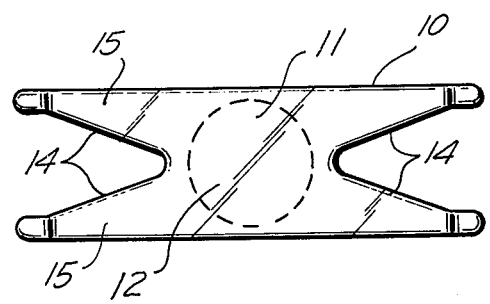
FIG. 1 is an anterior plan view of the lens of the present invention.
Figure 2:
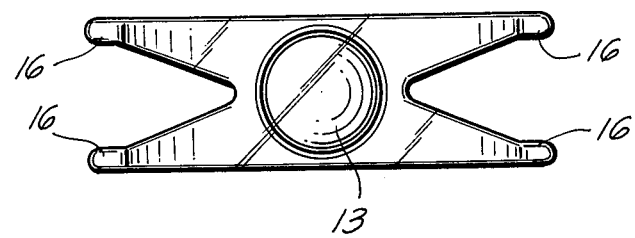
FIG. 2 is a posterior plan view of the lens of the present invention.
Figure 3:
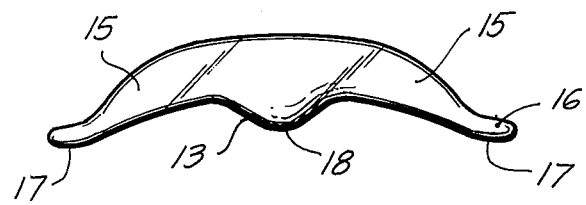
FIG. 3 is a side elevational view of the lens of the present invention.

Referring to the drawings which illustrate a preferred embodiment of the invention, reference numeral 10 generally indicates the lens of the present invention. The lens includes a lens portion 11 having an anterior planar surface 12 and a posterior convex surface 13. Attached to the lens portion, preferably integrally, are four extensions 14 arranged in opposed pairs, each extension consisting of a haptic 15, which is preferably arcuately bent away from the planar surface toward the convex surface, and a locating foot 16 extending outwardly from the haptic and substantially parallel to the planar surface. The posterior surfaces 17 of the locating feet form a plane which is posterially beyond the apex 18 of the convex surface of the lens.

The haptics are preferably conically shaped.

The lenses may be constructed of glass or clear plastic such as polymethyl methacrylate.

In inserting the lens into the eye the lens is placed in the anterior chamber of the eye with the convex surface facing the posterior preferably in a horizontal positional along its long axis, but it may, if desired, be placed in a vertical or oblique position.

The four supporting (haptic) feet are positioned in the angles made by the scleral spur in front and the root of the iris behind.

The lens of the present invention has a spherical aberration which is about the same as that of the natural lens.

The arrangement of the haptics and the supporting feet serves to hold the lens firmly in place after insertion. If, however, any subsequent movement does occur the refracted pencil or rays is not affected as much as with presently used intraocular lenses.

Since the convex portion of the lens is in the posterior position, the lens is in a focusing position more closely to the position of a natural lens than the planar convex lenses which have the convex surface in the anterior position. This serves to focus more properly the image on the retina.

The structure of the lens of the present invention eliminates the use of clips around the iris or sutures through the iris, the means now in use, and thus erosion of or other damage to the iris is less with lenses of the present invention than with presently available intraocular lenses.

We claim:

1. An intraocular lens for insertion in the anterior chamber of the eye comprising a lens portion having an anterior planar surface and a convex posterior surface, four extensions attached to said lens portion, said extensions being arranged in opposed pairs, each of said extensions consisting of a haptic which is bent away from the planar surface to the convex surface and a locating foot extending outwardly from the haptic and substantially parallel to the planar surface, the posterior surfaces of the feet lying in a plane which is posteriorly beyond the apex of the convex surface.

2. An intraocular lens according to claim 1 wherein the four extensions and lens portion are of unitary construction.

3. An intraocular lens according to claim 2, wherein the haptics are arcuately bent.

* * * * *